United States Patent [19]

Al-Hassan

[11] Patent Number: 5,658,594

[45] Date of Patent: *Aug. 19, 1997

[54] METHOD OF PRODUCING WOUND HEALING PREPARATION

[76] Inventor: Jassim M. Al-Hassan, c/o Kuwait University, Biochemistry Dept., P.O. Box 5969, 13060 Safat,, Kuwait

[*] Notice: The terminal 70 months of this patent has been disclaimed.

[21] Appl. No.: 944,941

[22] Filed: Dec. 22, 1986

[51] Int. Cl.$^6$ .................................................. A61K 35/60

[52] U.S. Cl. ........................ 424/537; 424/571; 424/572; 424/574

[58] Field of Search ..................................... 424/537, 571, 424/572, 574

[56] References Cited

PUBLICATIONS

Al–Hassan et al, Comp. Biochem. Physiol. 85B, 41–47 (1986).
Al–Hassan et al, Toxicon 24, 1009–1014 (1986).
Thompson et al, General Enzymes 111 (5112–5115) Fed. Proc., 41, 1145 (1982), No. 5112.
Thompson et al, Action of Toxins, Fed. Proc., 43, 1953, (1984) No. 3115.
Al–Hassan et al, Actions of Toxins, Fed. Proc., 43, 1952 (1984), No. 3112.
Al–Hassan et al, Lipoproteins II (1524–1529), Fed. Proc. 42, 2018 (1983) No. 1529.
Al–Hassan et al, Marine Biology 70, 27–33 (1982).
Thulesius et al, Gen. Pharmac. 14, 129–132 (1983).
Al–Hassan et al, Lancet, May 7, 1983, 1043–1044 (1983).
Al–Hassan et al, Toxicon 23, 532–534 (1985).
Al–Hassan et al, Marine Biology 88, 117–123 (1985).
Al–Hassan et al, Comp. Biochem. Physiol. 85B, 31–39 (1986).
Thompson et al, Lectins, Mitogens (1500–1505), Fed. Proc. 42, 2014 (1983) No. 1504.

*Primary Examiner*—Jean C. Witz

[57] ABSTRACT

A method of producing a wound healing preparation comprising shocking a club cell producing creature such as an Ariid catfish to stimulate secretion of the contents of such club cells, collecting the secreted materials by collecting epidermal materials of the creature as a gel.

20 Claims, No Drawings

METHOD OF PRODUCING WOUND HEALING PREPARATION

BRIEF DESCRIPTION OF THE INVENTION

1. Field of the Invention

This invention relates to collection, preparation and application of materials which, when applied to wounds in man or in animals, reduces healing times.

2. Background of the Invention

Wound repair in animals follows a well defined time coverage of sequential events, starting with clot formation and culminating with integration of newly synthesized cells and matrix components into the damaged tissue area. The time course of major events in the wound healing process has been described in studies from many laboratories. Healing in most "normal" cases is essentially complete in approximately ten days. However, a number of circumstances can greatly extend this time, including infections, nutritional deficiencies, metabolic conditions such as diabetes, genetic defects such as blood clotting factor deficiencies, and advanced age of the victim.

Many procedures and/or applications have been proposed to enhance healing rates. Antimicrobial agents help healing by blocking infections, but these may in some instances also interfere with cellular processes required for wound healing and cause some retardation of rates. Mechanical procedures to insure wound closure, including suturing or bandaging may speed recovery and help prevent excess scar tissue deposition. Chemical treatments with potential stimulatory action on various of the wound healing steps have been utilized with some success, but individual chemical or biochemical agents may be expected to have modes of action on only a limited number of processes within the complex scheme of wound healing reactions, without necessarily stimulating the total process. A number of synthetic or naturally occurring mixtures of components have been proposed in the past to contain a mixture of constituents which are generally stimulatory to the healing process. Convincing evidence supporting these claims and scientific evidence suggesting a physiological basis for the proposed stimulations are lacking.

U.S. Pat. No. 4,296,099 discloses a process for extracting embroyonic calf skin which comprises initially grinding the calf skin, extracting the same, and separating the resulting extract and lyophilizing the separated extract to provide an extract which exhibits cicatrisive activity and that is employed in cosmetic and pharmaceutical compositions.

So far as we are aware, however, there has not been proposed, fish epidermal preparations, nor methods of collecting and processing such preparations in the stimulation of wound healing.

OBJECTS OF THE INVENTION

Principal objects of the present invention are to provide for processing of a preparation from the epidermis of fish and particularly catfish and even more particularly from Ariid catfish that can be safely applied to the wound of an animal or human and that will stimulate wound healing.

Other objects are to provide a method of collecting materials from the epidermis of fish for use in treatment of wounds.

Still other objects are to provide a method of processing materials collected from an epidermis of a fish to make the same suitable and safe for use on wounds of humans and animals.

FEATURES OF THE INVENTION

Principal features of the invention include the shocking of the fish to stimulate the release of epidermal materials and in particular filamentous protein coils from the club cells which form a portion of the cellular structure of the fish epidermis.

Other features include the collection of the epidermal materials from the fish and the processing, including sterilization, of the collected secretions to make the preparation safe and viable for use on wounds of humans and other animals.

Additional objects and features of the invention will become apparent to those skilled in the pertinent art from the following detailed description.

DETAILED DESCRIPTION

It has been found that the application of certain fish epidermal preparations to wounds appears to act quite generally in stimulating all observed phases of the healing process. The complex mixture of pharmacologically active components in the preparation thus appears to contain a balanced combination of stimulatory agents which influence the entire healing process. This is supported by both histological and biochemical observations. Many of the active constituents of the preparation have now been isolated and their modes of action in healing have been documented. These provide a clear indication of how the preparation can function to stimulate healing.

It has been observed that Ariid catfish, when threatened or injured or otherwise shocked, secrete a proteinaceous, gel-like mixture from unicellular glands, which are frequently termed club cells. This material, together with some additional epidermal components, is collected by gentle mechanical scraping, or suction, from the epidermal surfaces. The collected material has a gel-like consistency and will be referred to as epidermal gel. The gel is immediately chilled or frozen to limit microbial growth. The total gel preparation may be used for application to wounds, but further fractionation and purification of components is commonly employed to provide a safer, more viable preparation for use on wounds. Shocking of the fish can result from thermal shock, physical abrasions or neural stimulation.

The catfish as well as many additional fish species, have club cells in the epidermis. Epidermal preparations from these other species will contain some components analogous to the major constituents of the Ariid catfish secretion, but these will be more difficult to obtain in a form separated from the bulk of epidermal materials.

Fractionation and purification of a soluble fraction of the Ariid epidermal gel is by homogenization of the total gel with dilute saline, followed by centrifugation. The soluble gel fraction is sterilized by membrane filtration or ultrasound treatment. Soluble protein fraction may be stored either frozen, preferably at −80° C. Soluble gel fraction may be applied directly to wounds to enhance healing.

The soluble gel may be fractionated further to yield active proteins and lipids which have effects on wound healing as described below. These are active individually in enhancing various steps of the wound healing processes. They may be recombined to reconstitute general activity.

A summary of some active constituents of soluble gel which have been identified, to date, as affecting specific healing characteristics as identified below (A through G) is as follows:

A. Clotting Factor. A high molecular weight protein (500,000 g/M) catalyzes conversion of blood clotting Factor X to Xa. Active Factor Xa then catalyzes production of thrombin and subsequently the formation of the fibrin clot. The soluble gel clotting factor is a calcium dependent serine protease with specificity similar to that of normal blood proteases causing activation of Factor X.

B. Lectin. A galactose specific lectin protein (200,000 molecular weight) accounts for about 2% of the soluble protein. This protein causes agglutination of human types A, B, and O red blood cells. It is capable of recognition of galactose moieties on the surface of cells and may aid in wound closure and adhesion of injured surfaces.

C. Lytic Enzymes. The gel contains a number of hydrolytic components. There is an active hemolytic protein which induces lysis of red blood cells. Proteolytic activity is very low in the crude preparation, but is noted in partially purified preparations, indicating removal of endogenous protease inhibitors. There are at least four esterases present in the preparation. Phosphatase activity is present and will be discussed in detail later. No lipase activity is measurable.

D. Phosphorylases. A family of phosphorylases is present in the soluble gel protein mixture. These include (a) a tyrosine phosphorylase, (b) phosphorylase(s) which appear to generally phosphorylate many of the gel proteins or added plasma membrane proteins at serine, threonine and tyrosine residues, and (c) an enzyme which phosphorylates phosphatidyl inositol.

E. Platelet Activating Factors. The epidermal preparation contains a family of 1-0-alkyl-2-sn-acetyl glycerolphosphatidyl choline molecules, with alkyl chain lengths varying from 15 to 24 carbons, which stimulate activation of platelets. These are present at levels 5000 times those commonly found in animal sources.

F. Prostaglandins. The epidermal gel preparation contains low levels of prostaglandins, and in addition is able to induce formation of high levels of prostaglandins via stimulation of endothelial cells or epidermal cells.

G. Smooth Muscle Contraction. The epidermal preparation contains at least two components which stimulate contraction of smooth muscle. One is blocked by cyclooxigenase inhibitors, and the other by atrophine.

The benefits of an externally added clotting factor in aiding wound healing are readily apparent. The first step in wound healing is clotting. Clot formation initiates a number of important metabolic events which stimulate cell metabolism and initiate cell proliferation. Primary among these is platelet activation. The high level of platelet activating factors found in the epidermal preparation also rapidly induces platelet activation in a wound area. Among the results of this activation are secret from the platelets of serotonin, platelet derived growth factor, and other biochemicals. Serotonin aids vasoconstriction, shutting down the flow of blood to the wound area. Platelet derived growth factor (PDGF) is both chemotactic and mitogenic for fibroblasts, thus it aids in promoting the movement of these collagen producing cells into the wound area and induces their proliferation. The products of the fibroblasts are major components needed for tissue repair. Platelet activation also stimulates hydrolysis of phospholipids and release of inositol phosphates. These inositol compounds regulate calcium levels in the cells and alter cell metabolism.

Phosphorylase action directed by the epidermal preparation has stimulatory activity at several levels in cell metabolism. Direct phosphorylation of phosphatidyl inositol to the di- and triphosphate forms stimulates as described above. In addition, an endogenous inhibitor protein of phospholipase A2 in epidermal membranes is phosphorylated, resulting in deactivation of the inhibitor and expression of the lipase activity. The lipase catalyzes release of arachadonic acid. Arachadonic acid is rapidly converted to prostaglandins which regulate many cellular processes in the wound area. For example, prostaglandins affect inflammatory responses, pain responses, migration of cells into the wound area, angiogenesis and rates of cell proliferation. All of these processes are key steps in wound healing.

Lytic enzymes from the epidermal secretion may play important roles in break down of damaged cells. No definite role has yet been established for the lectin present in the epidermal secretion. Lectins have in general been postulated to serve as important elements in cellular adhesion. The epidermal gel preparation does promote a rapid adhesion of wound tissues. The lectin is a likely candidate for this action as it may recognize and bind galactose moieties on adjacent cell surfaces to give the noted adhesion.

Although a preferred form of our invention has been herein disclosed, it is to be understood that the present disclosure is by way of example and that variations are possible without departing from the subject matter coming within the scope of the following claims, which subject matter we regard as our invention.

I claim:

1. A method of producing a wound healing composition comprising the steps of
    shocking an Ariid catfish to stimulate secretion of an epidermal gel;
    collecting the epidermal gel secreted by said catfish.

2. The method as in claim 1, wherein the shocking of said catfish further comprises at least one of hooking said catfish, catching said catfish in a trawl net, changing the temperature of water surrounding said catfish, changing the pressure of water surrounding said catfish, and applying electric shock to said catfish.

3. The method as in claim 1, wherein the shocking of said catfish comprises thermal shock.

4. The method as in claim 1, wherein the shocking of said catfish comprises neural shock.

5. The method of claim 1, wherein said collecting further comprises scraping said catfish.

6. The method as in claim 1, wherein said collecting further comprises suctioning said gel.

7. The method as in claim 1, further comprising sterilizing said gel.

8. The method as claimed in claim 1, further comprising freezing said gel after said collecting.

9. A composition for aiding in the treating of wounds and skin lesions comprising a would healing effective amount of sterilized epidermal gel secretions from the skin of an Ariid catfish.

10. A composition for aiding in the treatment of wounds and skin lesions comprising a wound healing effective amount of the composition produced according to claim 1.

11. A composition for aiding in the treatment of wounds and skin lesions comprising a wound healing effective amount of the composition produced according to claim 2.

12. A composition for aiding in the treatment of wounds and skin lesions comprising a wound healing effective amount of the composition produced according to claim 5.

13. A composition for aiding in the treatment of wounds and skin lesions comprising a wound healing effective amount of the composition produced according to claim 7.

14. A composition for aiding in the treatment of wounds and skin lesions comprising a wound healing effective amount of the composition produced according to claim 8.

15. The method of claim 1, further comprising homogenizing said gel with dilute saline, centrifuging said gel to form a supernatant and sterilizing said supernatant.

16. The method of claim 15, wherein said sterilizing comprises filtering said supernatant through a membrane.

17. The method of claim 8, further comprising homogenizing said gel with dilute saline, centrifuging said gel to form a supernatant and sterilizing said supernatant.

18. The method of claim 17, wherein said sterilization comprises filtering said supernatant through a membrane.

19. A composition for aiding in the treatment of wounds and skin lesions comprising a wound healing effective amount of the composition produced according to claim 16.

20. A composition for aiding in the treatment of wounds and skin lesions comprising a wound healing effective amount of the composition produced according to claim 18.

* * * * *